United States Patent
Kim et al.

(10) Patent No.: US 11,737,674 B2
(45) Date of Patent: Aug. 29, 2023

(54) RF MICROWAVE CORE TEMPERATURE SYSTEM HAVING RF RECEIVER MODULE TO DETECT CORE TEMPERATURE

(71) Applicant: EASYTEM Co., Ltd., Siheung-si (KR)

(72) Inventors: Nam Young Kim, Gwangju-si (KR); Eun Seong Kim, Gwangju-si (KR); Jaewoo Shin, Seoul (KR)

(73) Assignee: EASYTEM Co., Ltd., Siheung-si (KR)

( * ) Notice: Subject to any disclaimer, the term of this patent is extended or adjusted under 35 U.S.C. 154(b) by 308 days.

(21) Appl. No.: 17/169,447

(22) Filed: Feb. 6, 2021

(65) Prior Publication Data

US 2022/0192504 A1    Jun. 23, 2022

(30) Foreign Application Priority Data

Dec. 20, 2020    (KR) .................. 10-2020-0179132

(51) Int. Cl.
*A61B 5/01*    (2006.01)
*G01K 1/024*    (2021.01)
(Continued)

(52) U.S. Cl.
CPC ............. *A61B 5/01* (2013.01); *A61B 5/0022* (2013.01); *A61B 5/05* (2013.01); *A61B 5/7203* (2013.01);
(Continued)

(58) Field of Classification Search
CPC ........... A61B 5/01; A61B 5/0022; A61B 5/05; A61B 5/7203; A61B 5/7435;
(Continued)

(56) References Cited

U.S. PATENT DOCUMENTS 5,176,146 A * 1/1993 Chive ................. G01K 11/006
                                                374/E11.003
2009/0187115 A1* 7/2009 Yarden .................. G01K 13/20
                                                600/549
(Continued)

FOREIGN PATENT DOCUMENTS

KR      20020074920 A    10/2002

OTHER PUBLICATIONS

Robert Patterson Scheeler, "A Microwave Radiometer for Internal Body Temperature Measurement", A thesis submitted to the Faculty of the Graduate School of the University of Colorado in partial fulfillment of the requirements for the degree of Doctor of Philosophy Department of Electrical, Computer, and Energy Engineering, 2013, (189 Pages total).

(Continued)

*Primary Examiner* — Nathaniel T Woodward
*Assistant Examiner* — Philip L Cotey
(74) *Attorney, Agent, or Firm* — Sughrue Mion, PLLC

(57) ABSTRACT

Provided are a radio frequency (RF) receiver module for sensing core body temperature and an RF microwave core body thermometer system having the same. The RF receiver module for sensing core body temperature and the RF microwave core body thermometer having the same include: an RF contact-type patch antenna attached to a body part to sense the core body temperature; an RF receiver circuit unit attached to the body part to receive any one RF frequency signal within an RF frequency range of 1 to 10 GHz except for 1.4 GHz, 1.6 GHz, 1.7 GHz, 2.6 GHz and 2.7 GHz through the RF contact-type patch antenna for sensing core body temperature; and an interface circuit unit for connecting the RF receiver circuit unit to a control unit of a microprocessor control unit.

13 Claims, 12 Drawing Sheets

(51) Int. Cl.
*A61B 5/05* (2021.01)
*A61B 5/00* (2006.01)
*G01K 1/02* (2021.01)
*G01K 11/00* (2006.01)
*A61B 5/0507* (2021.01)

(52) U.S. Cl.
CPC .............. *A61B 5/7435* (2013.01); *G01K 1/024* (2013.01); *G01K 1/028* (2013.01); *G01K 11/006* (2013.01); *A61B 5/002* (2013.01); *A61B 5/0008* (2013.01); *A61B 5/0507* (2013.01); *A61B 5/6823* (2013.01); *A61B 5/6833* (2013.01); *A61B 5/7225* (2013.01); *A61B 5/7445* (2013.01); *A61B 2560/0214* (2013.01); *A61B 2562/0228* (2013.01); *A61B 2562/0271* (2013.01)

(58) Field of Classification Search
CPC ..... A61B 5/0008; A61B 5/002; A61B 5/0507; A61B 5/6823; A61B 5/6833; A61B 5/7225; A61B 5/7445; A61B 2560/0214; A61B 2562/0228; A61B 2562/0271; G01K 1/024; G01K 1/028; G01K 11/006
See application file for complete search history.

(56) References Cited

U.S. PATENT DOCUMENTS

| | | | |
|---|---|---|---|
| 2010/0069782 A1* | 3/2010 | Icove | G01K 11/006 600/549 |
| 2011/0176578 A1* | 7/2011 | Zei | A61B 5/0507 374/E11.001 |
| 2012/0029369 A1* | 2/2012 | Icove | G01K 13/20 600/504 |
| 2017/0340208 A1* | 11/2017 | Popovic | A61B 5/01 |
| 2018/0058945 A1* | 3/2018 | Vesnin | A61B 5/0507 |
| 2021/0219846 A1* | 7/2021 | Allison | G01K 13/20 |
| 2022/0079438 A1* | 3/2022 | Baek | A61B 5/6833 |
| 2022/0167865 A1* | 6/2022 | Tofighi | A61B 5/0075 |
| 2022/0361810 A1* | 11/2022 | Price | A61B 5/7405 |

OTHER PUBLICATIONS

Communication dated Mar. 8, 2021, from the Korean Intellectual Property Office in application No. 10-2020-0179132.
Communication dated Mar. 8, 2021, from the Korean Intellectual Property Office in application No. 10-2020-0184032.
Communication dated Feb. 24, 2021, from the Korean Intellectual Property Office in application No. 10-2020-0170917.

* cited by examiner

RF MICROWAVE CORE TEMPERATURE SYSTEM HAVING RF RECEIVER MODULE TO DETECT CORE TEMPERATURE

CROSS-REFERENCE TO RELATED APPLICATION

This application claims priority to Korean Patent Application No. 10-2020-0179132, filed on Dec. 20, 2020, in the Korean Intellectual Property Office, the disclosure of which is herein incorporated by reference in its entirety.

FIELD

The present invention relates to an RF microwave core body thermometer, and more particularly, to an RF microwave core body thermometer system having an RF receiver module, in which one MMIC chip is manufactured by using a CMOS process on a silicon (Si) substrate as one chip in the RF receiver module for a core body thermometer in order to manufacture the RF microwave core body thermometer having an RF receiver module (an RF/IF receiver module) for sensing core body temperature, and core body temperature inside a human body is measured using any one RF frequency signal within an RF frequency range of 1 to 10 GHz.

BACKGROUND

Conventional core body temperature measurement methods that non-invasively measure core body temperature of a living body or a human body include a magnetic resonance imaging (MRI) temperature imaging method, an ultrasonic temperature measurement method, an impedance temperature measurement method, a human body radiation microwave measurement method (microwave radiometry), and the like. Among these methods, the microwave radiometry has been actively studied by a large number of researchers in the United States, Japan, Germany, and Italy.

As prior technique 1 related thereto, "Method and device for measuring inside temperature of a living body using microwave" is disclosed in Korean Patent Publication No. 10-2002-0074920.

FIG. 1 is a block diagram showing a conventional device for measuring core body temperature of a living body using microwaves.

The device for measuring core body temperature of a living body using microwaves includes: a signal receiving unit for receiving microwaves radiated from a living body and outputting the microwaves; a signal processing unit for measuring a surface temperature of the living body from the microwaves output from the signal receiving unit, and outputting the measured surface temperature; a weighting value estimation unit for estimating a weighting value corresponding to medium characteristics of a corresponding part of the living body from which the microwaves are emitted, and outputting the estimated weighting value; and a temperature conversion unit for measuring core body temperature of the living body from the weighting value input from the weighting value estimation unit and the surface temperature input from the signal processing unit.

As a block diagram, a device for measuring core body temperature of a living body using microwaves comprises a signal receiving unit 10, a signal processing unit 12, a weighting value estimation unit 14, and a temperature conversion unit 16.

A method of measuring core body temperature of a living body measures a core body temperature of a living body by using a surface temperature measured from microwaves received from the signal receiving unit 10 and a weighting value that can be changed by the medium characteristics of a measured part.

The signal receiving unit 10 receives microwaves of a specific frequency band radiated from an arbitrary part of a living body, of which the temperature is to be measured, through an input terminal IN1, and outputs the received microwaves to the signal processing unit 12 (step 20). To this end, the signal receiving unit 10 may be provided with an antenna or a probe and a transmission line capable of receiving the microwaves radiated from the living body.

After step 20, a surface temperature (or brightness temperature) of the living body is measured from the received microwaves, and a weighting value corresponding to the medium characteristics of the corresponding part of the living body, from which the microwave is radiated, is estimated (step 22).

To this end, the signal processing unit 12 measures the surface temperature of the living body from the microwaves output from the signal receiving unit 10 and outputs the measured surface temperature to the temperature conversion unit 16.

FIG. 1b is a block diagram showing a signal processing unit, and FIG. 1c is a view showing a genome model of a biological tissue. In an embodiment of the signal processing unit 12 includes a noise removing unit 30, a filter 32, an amplifier 34, and a control unit 36.

The noise removing unit 30 of the signal processing unit 12A inputs the microwaves received from the signal receiving unit 10 through an input terminal IN4 to remove noise, and outputs a result of removing the noise to the filter 32. At this point, the filter 32 filters a desired band from the result of removing the noise output from the noise removing unit 30 and outputs the filtered result to the amplifier 34. The amplifier 34 amplifies the output of the filter 32 and outputs the amplified result to the control unit 36. The control unit 36 measures a surface temperature from the result amplified by the amplifier 34, and outputs the measured surface temperature to the temperature conversion unit 16 through an output terminal OUT2.

In addition, the weighting value estimation unit 14 estimates a weighting value corresponding to the medium characteristics of a corresponding part of the living body from which the microwaves are radiated, and outputs the estimated weighting value to the temperature conversion unit 16.

As a block diagram of an embodiment 14A of the weighting value estimation unit 14, it is configured of a medium characteristic measurement unit 40 and a weighting value correction unit 42.

The medium characteristic measurement unit 40 of the weighting value estimation unit 14A measures medium characteristics through the input terminal IN2, and outputs the measured medium characteristics to the weighting value correction unit 42. To this end, the medium characteristic measurement unit 40 may provide a skin-fold caliper, a bio impedance analyzer, an ultrasonic skinfold caliper (ultrasound fat meter), a magnetic resonance imaging (MRI) scanner, or a microwave tomography (microwave computed tomography) as a sensing unit (not shown) for sensing the medium characteristics. For example, the skin-fold caliper may be implemented as a product named "Fat Control Skinfold Caliper" manufactured by "FAT CONTROL, INC" in the United States, and the bio impedance analyzer may be implemented as a body fat analyzer (model number: GIF-891DXH) sold by COMEDICAL, which is a medical device manufacturer, and the ultrasonic skinfold caliper may be implemented as an ultrasonic skinfold caliper (model name: AFT-101G) sold by Titlemedia.

When the sensing unit (not shown) of the medium characteristic measurement unit 40 is implemented as a bio impedance analyzer, an ultrasonic skinfold caliper, or a microwave tomography, the sensing unit (not shown) of the medium characteristic measurement unit 40 may be implemented to be integrated with the sensing unit that receives microwaves from the signal receiving unit 10.

At this point, the weighting value correction unit 42 corrects the weighting value to match the medium characteristics measured by the medium characteristic measurement unit 40, and outputs the corrected weighting value to the temperature conversion unit 16 through the output terminal OU3 as an estimated weighting value. Here, the weighting value correction unit 42 may operate online to directly output the estimated weighting value to the temperature conversion unit 16, or may operate offline to adjust the estimated weighting value in response to an adjustment control signal input from the outside through the input terminal IN5, and output the adjusted weighting value to the temperature converter 16, to calibrate the characteristics of the temperature measurement device shown in FIG. 1.

FIG. 1c is a view showing a genome model of a biological tissue and is configured of skin 60, fat 62, and muscle 64.

For example, when each part of a living body is modeled as skin 60, fat 62 and muscle 64, permittivity ($\epsilon 1$, $\epsilon 2$ and $\epsilon 3$) of the modeled skin 60, fat 62 and muscle 64 and the thicknesses d1, d2 and d3 of the dielectrics 60, 62 and 64 may be different from each other by a living body to be measured, each part of the living body, or a temperature measurement environment.

As described above, although the permittivity and the thickness change by a given condition, the conventional core body temperature measurement methods measure core body temperature of a living body by using a fixed weighting value. However, the method and device for measuring core body temperature of a living body modifies the weighting value by the characteristics of a medium, e.g., permittivity $\epsilon 1$, $\epsilon 2$ and $\epsilon 3$ and thicknesses d1, d2 and d3, that change by a given condition.

For example, in the case where d2≈10 mm and d2≈20 mm, the weighting value estimation unit 14 measures fat thickness d2 of a living body, and when the measured fat thickness d2 is approximately 10 mm, the weighting value estimation unit 14 determines a weighting value using a graph and outputs the determined weighting value to the temperature conversion unit 16 as an estimated weighting value. In addition, when the measured fat thickness d2 is approximately 20 mm, the weighting value estimation unit 14 determines a weighting value using a graph and outputs the determined weighting value to the temperature conversion unit 16 as an estimated weighting value.

The temperature conversion unit 16 measures core body temperature of a living body from the weighting value input from the weighting value estimation unit 14 and the surface temperature input from the signal processing unit 12, and outputs a measured core body temperature through the output terminal OUT1 (step 24). For example, the temperature conversion unit 16 may measure core body temperature [T(z)] of a living body as shown below in Equation 1.

$$T(z)=T_0+T_1(1-e^{-z/a})+T_2 z/be^{-z/b}$$ Equation (1)

Here, $T_0$, $T_1$, and $T_2$, a and b are parameters that determine core body temperature of a living body, are determined by the surface temperature output from the signal processing unit 12 and the weighting value output from the weighting value estimation unit 14, and become 0≤z≤∞. An exemplary method of determining the various parameters ($T_0$, $T_1$, and $T_2$, a and b) from the surface temperature and the weighting value is described in pages 236 and 237 of a book written by 'Michio Miyakawa, J. Ch. Bolomey' and published by CRC Press in 1996 under the title of "Non-invasive thermometry of the Human Body".

For example, when the thickness d2 of the fat is approximately 10 mm, the surface temperature is 38.2° C., and when the thickness d2 of the fat is approximately 20 mm, the surface temperature is 37.05° C. Like this, when the surface temperature has a difference of about 1.14° C. in accordance with the thickness d2 of a modeled fat tissue, the temperature conversion unit 16 may accurately measure the core body temperature of a living body by reflecting a small change in the surface temperature and the weighting value into the parameters.

FIG. 2 shows an infrared temperature measurement method: (a) a forehead-type infrared thermometer, (b) a picture of an infrared thermal imaging camera.

Conventional body temperature measurement methods use an infrared sensor, and a thermopile sensor is used for single spot measurement, and a bolometer sensor is used for thermal image measurement.

However, since temperature measurement using an infrared sensor is measuring the wavelength of thermal infrared rays emitted from the skin, which is the surface of a human body, and it measures skin temperature, not core body temperature, of an actual human body, measurement of skin temperature of the infrared thermometer may not accurately reflect the core body temperature as shown in FIG. 3 as the skin temperature is different in each human body part.

In the method of measuring skin temperature of an infrared thermometer, for example, skin temperature of each part of a human body, such as a forehead, a nose, a chin, a chest, an arm, a side, or a leg, is differently measured by the infrared thermometer. Since the skin temperature of the body changes as ambient temperature changes, deviation thereof is shown to be differently in accordance with body parts, and the skin temperature deviates according to individual differences in the skin color or skin condition.

FIG. 4 is a view showing changes in the skin temperature and the core body temperature according to increase in the volume of body exercise. A radiometer and a contact-type antenna (near-field probe) measure core body temperature of a human body using an RF frequency signal, and an infrared thermometer (thermocouple) measures skin temperature by measuring the wavelength of thermal infrared rays radiated from the surface skin of a human body, and the core body temperature and the skin temperature are output to the display unit of the radiometer by temperature retrieval software.

Generally, in the case of the forehead area that is widely used by an infrared thermometer, the temperature of the forehead varies up to about 3° C. difference whenever the ambient temperature varies as much as 10° C. although deviation of temperature is small compared to those of other skin areas due to the temporal arteries distributed under the forehead.

For example, assuming that the temperature in summer is 30° C. and the temperature in winter is 15° C., deviation of the ambient temperature is 15° C., so that although the body temperature is constant, temperature measured on the skin has a difference of about 4.5° C., and thus accurate measurement of core body temperature is impossible.

When a person runs during an exercise, as the exercise volume of the human body increases actually momentum (p=mv), core body temperature rises, and secretion of sweat is accelerated in the skin to cool down the core body temperature, and the skin temperature decreases due to the sweat. Therefore, the infrared thermometer (thermocouple) that measures skin temperature determines that the skin temperature decreases although the core body temperature increases.

Domestic R&D Status

* Although a basic research paper on the technique of measuring biological temperature using RF microwaves has been released in 2005, there is no cases of publishing thesis or academic journals on the subject since then up to now.

* Tae-O Kim et al. have measured central temperature of distilled water and a mixed solution through a modified microwave radio-thermometer for measuring temperature of a living body (March 2005, Journal of the Institute of Electronics and Information Engineers, Vol. 42, No. 2), showing a measurement error of up to 0.82 to 7.68° C.

* Kyung-Ryeol Choi et al. of Korea Institute of Industrial Technology have applied for 3 patents on "Microwave temperature measurement technique capable of measuring temperature of internal heat source" ("Method and device for measuring core body temperature using microwaves", "Method and device for measuring core body temperature based on microwaves using frequency of maximum amplitude", "Method and device for measuring core body temperature based on microwaves using a plurality of frequencies of multiple channels") in 2009 and 2010, and presented a technique of an idea establishing step corresponding to TRL1 and TRL2 in the technology readiness level.

* Although Samsung Electronics has presented the possibility of measuring temperature inside a living body through a test using a human phantom by applying for a patent related to "Radio-thermometer for measuring electromagnetic waves inside a human body, and method of measuring electromagnetic waves in human body" together with Russian Microwave Research Institute in 2003, the patent is abandoned and extinguished due to lack of specific design and process techniques of related technologies.

As described above, it is an unexplored field in Korea, in which there are few R&D cases yet, and cases of publishing research papers including patents are poor, and there are no specific research cases for commercialization.

Overseas R&D Status

* Russian RES Company has released a product called RTM-01-RES although it is not for being used as a thermometer, and it employs a microwave temperature measurement method for the purpose of diagnosing breast cancer.

* The RES's breast cancer diagnosis device is used for diagnosis by measuring temperature of a breast tissue at a depth of about 5 cm from the skin, inspired by the fact that temperature of a lesion of a cancer cell is higher than temperature of other tissues surrounding the cancer cell. However, it is constructed in a limited structure of contacting an electrode in the shape of a bar.

* Parisa Momenroodaki, Zoya Popovic, Robert Scheeler, A 1.4-GHz radiometer for core body temperature measurements, Physics, 2015 European Microwave Conference (EuMC)

For the sake of non-invasive core body temperature measurement of penetrating several centimeters into the internal tissues of a human body, a microwave radiometer circuit applying a frequency of 1.4 GHz is implemented to measure water temperature at a sensitivity of 0.5K.

* The paper "A High Accuracy Microwave Radiometric Thermometer to Measure Core body temperature" published by Michael Grady in Materials Science in 2017 has analyzed penetration depth of microwaves penetrating in accordance with various RF frequency bands, and presented a model related to penetration.

* The paper "A microwave radiometer for close proximity core body temperature monitoring: Design, development, and experimentation" published by Quenton Bonds in 2010 in Engineering has presented a structure of an efficient dipole antenna for measuring core body temperature inside a human body, and analyzed response characteristics.

* The paper "Antenna probes for power reception from deep tissues for wearable microwave thermometry" published by P. Momenroodaki, Z. Popovic and M. Fallahpour in IEEE International Symposium on Antennas and Propagation & USNC/URSI National Radio Science Meeting, San Diego, Calif., 2017, pp. 573-574 has designed and presented a wearable antenna probe for monitoring core body temperature inside a human body by using a 1.4 GHz microwave radiation measurement method, and a probe having superstrates to maximize the volume loss power density in a specific buried layer.

* The paper "Non-invasive Core body temperature Tracking With Near-Field Microwave Radiometry" published by P. Momenroodaki, W. Haines, M. Fromandi, and Z. Popovic in IEEE Transactions on Microwave Theory and Techniques, vol. 66, no. 5, pp. 2535-2545, May 2018 has proved that the study on near-field radiation measurement for measuring core body temperature of a human body has a Dicke architecture and traces temperature of a phantom muscle tissue layer underneath some degree of phantom fat and skin layers by using 1.4 GHz so as to penetrate into human tissues by the depth of centimeters while minimizing Radio Frequency Interference (RFI).

The paper "Non-invasive microwave thermometry of multilayer human tissues" published by P. Momenroodaki, W. Haines, and Z. Popovic in 2017 in IEEE MTT-S International Microwave Symposium (IMS), Honolulu, Hi., 2017, pp. 1387-1390 has shown that a radiometer may trace internal tissue temperature based on measurement data using a Dicke radiometer, by analyzing penetration characteristics in several tissue layers of skin, fat, and muscle in human tissues by using a narrow-band probe.

Particularly, the research team of Professor Z. Popovic of the University of Colorado used a compound semiconductor GaAs MMIC (monolithic microwave integrated circuit) technique for miniaturization of an RF microwave transceiver module that measures body temperature inside a human body, and attempted fabrication of a partial MMIC chip using a compound GaAs foundry of Tryquent Company. Since this partial MMIC chip fabrication does not implement an MMIC of an entire receiver, the efficiency of the receiving side is low, and there is a limit in measuring temperature according to the power of an accurate RF frequency.

Currently, blockade of each country due to the new coronavirus infection (Corona 19) has resulted in severance of global value chain (GVC). Korean companies need reshoring (returning to their home country) centering on industry of high technology innovation level and should localize advanced technologies, and in particular, self-sufficiency in medical device technologies for quarantine and diagnosis is needed more than ever.

In the case of thermometers, among the major countries such as Germany and China that produce infrared sensors, Germany and China take action to export restrictions on key infrared sensors to meet demand on infrared thermometers in Europe and in China. Although thermometer manufacturers in Korea entirely relying on import the infrared sensors are belatedly collaborating with companies that localize the infrared sensors, it is difficult to sufficiently supply the infrared thermometers.

In a situation where the overseas supply chain of the infrared thermometers has collapsed as described above, expansion of localization of infrared sensors for self-sufficiency of infrared thermometers may be an alternative. Basically, the infrared sensors do not overcome the fundamental limit of measuring skin surface temperature without advancement in technology over the past 30 years, and it needs to manufacture RF microwave core body thermometers.

(Patent Document 1) Korean Patent Publication No. 10-2002-0074920 (Publication date, Oct. 4, 2002), "Device and method for measuring core body temperature of a living body using microwaves", Samsung Electronics Co., Ltd.

SUMMARY

Therefore, the present invention has been made to solve the above problems, and an object of the present invention is to provide an RF receiver module for measuring core body temperature, in which one MMIC chip is manufactured by using a CMOS process on a silicon (Si) substrate as one MMIC chip in the RF receiver module for a core body thermometer in order to manufacture the RF microwave core body thermometer having an RF/IF receiver module, and core body temperature inside a human body is measured by using any one RF frequency signal within an RF frequency range of 1 to 10 GHz.

Another object of the present invention is to provide an RF microwave core body thermometer system having an RF receiver module for sensing core body thermometer.

To accomplish the above objects, according to one aspect of the present invention, an RF receiver module for sensing core body temperature includes: an RF contact-type patch antenna attached to a human body part to sense the core body temperature; an RF receiver circuit unit to receive any one RF frequency signal within a frequency range of 1 to 10 GHz except for 1.4 GHz, 1.6 GHz, 1.7 GHz, 2.6 GHz and 2.7 GHz through the RF contact-type patch antenna for sensing core body temperature and to be attached to a human body; and an interface circuit unit for connecting the RF receiver circuit unit to a control unit of a microprocessor control unit, wherein the interface circuit unit includes an A/D converter for receiving the in-phase signal LO_I and its quadrature signal LO_Q of a local oscillator LO received from the RF receiver circuit unit, and A/D converting the signals; and a temperature converter for converting a heat radiation signal into a core body temperature inside a human body.

To accomplish another object of the present invention, an RF microwave core body thermometer system having an one RF receiver module for sensing core body temperature includes: said one RF receiver module for sensing core body temperature, which receives any one RF frequency signal within an RF frequency range of 1 to 10 GHz except for 1.4 GHz, 1.6 GHz, 1.7 GHz, 2.6 GHz and 2.7 GHz; and an RF microwave core body thermometer connected to an interface circuit unit of said one RF receiver module in order to display a core body temperature inside the human body measured by the power corresponding to a frequency by using a basic principle that radiation intensity linearly changes at an RF frequency lower than 10 GHz with respect to a core body temperature inside the human body by a Planck's law, on an OLED display using the received RF frequency signal.

wherein said one RF receiver module for sensing core body temperature, being included in an RF microwave core body thermometer, the module comprising; an RF contact-type patch antenna attached to a human body part to sense the core body temperature of the human body; an RF receiver circuit unit to receive any one RF frequency signal within a frequency range of 1 to 10 GHz except for 1.4 GHz, 1.6 GHz, 1.7 GHz, 2.6 GHz and 2.7 GHz through the RF contact-type patch antenna for sensing core body temperature and to be attached to a human body; and an interface circuit unit for connecting the RF receiver circuit unit to a control unit of a microprocessor control unit, wherein the thermometer further includes a handy-type body equipped with the RF microwave core body thermometer having the RF receiver module, connected to an interface circuit of the RF receiver module, driven by a lithium polymer battery, included with an LED indicator, included with a color OLED display and a button input unit on the top surface, and included with a measurement shot button of the handle of the pistol-shaped handy-type body.

DETAILED DESCRIPTION

Hereinafter, the configuration and operation of the example embodiments of the present invention will be described in detail with reference to the accompanying drawings.

The present invention manufactures one MMIC chip on a silicon (Si) substrate by using a CMOS process as one chip in the RF receiver module for a core body thermometer, and provides an RF microwave core body thermometer equipped with an RF receiver module (RF/IF Si MMIC receiver module) for sensing core body temperature, which measures core body temperature of a human body by using any one RF frequency signal within an RF frequency range of 1 to 10 GHz except for 1.4 GHz, 1.6 GHz, 1.7 GHz, 2.6 GHz and 2.7 GHz.

Figure 1A:
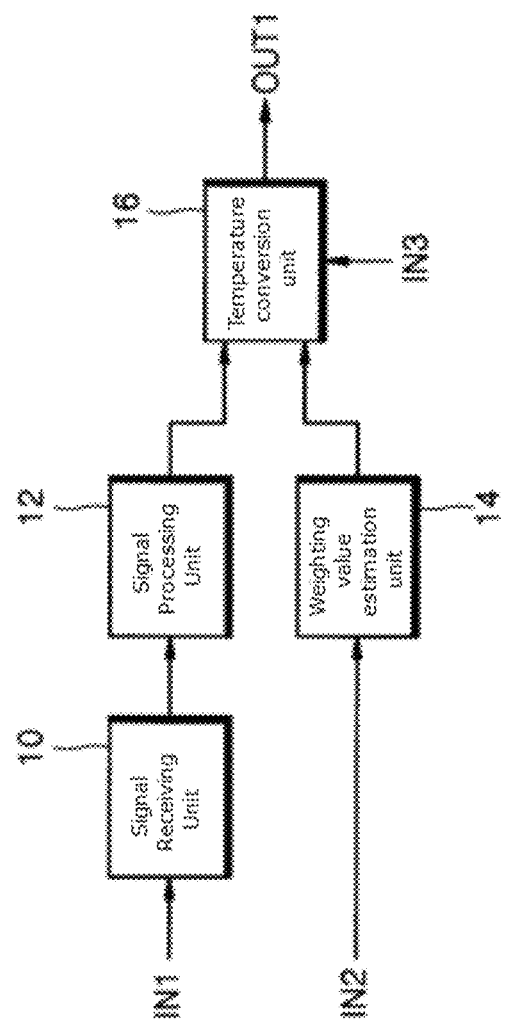
FIG. 1a is a block diagram showing a conventional device for measuring core body temperature of a living body using microwaves.
Figure 1B:
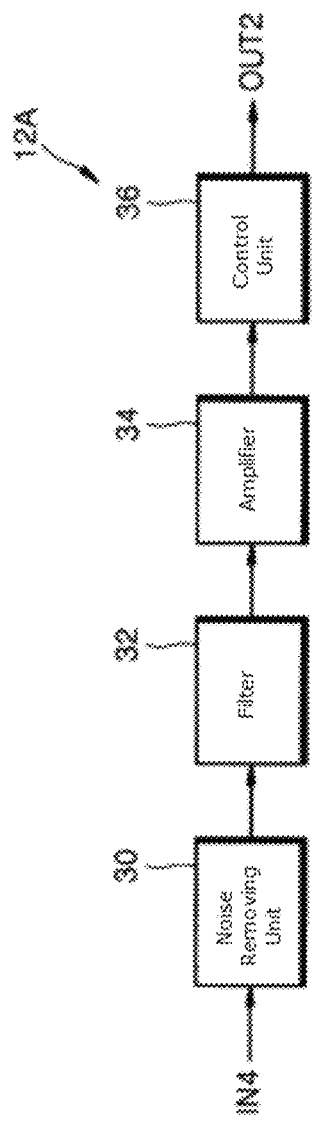
FIG. 1b is a block diagram showing a signal processing unit.
Figure 1C:
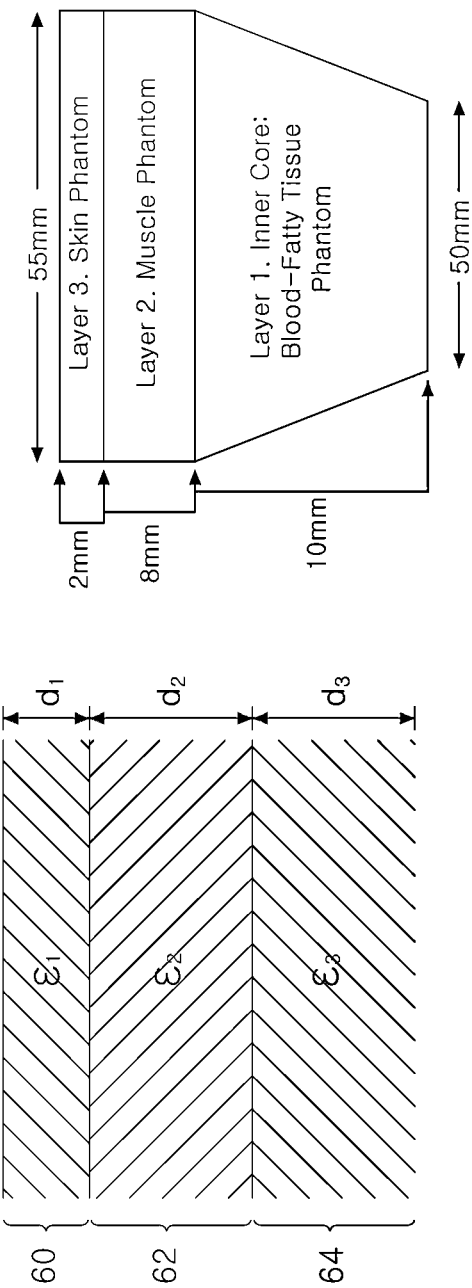
FIG. 1c is a view showing a genome model of a biological tissue.
Figure 2:
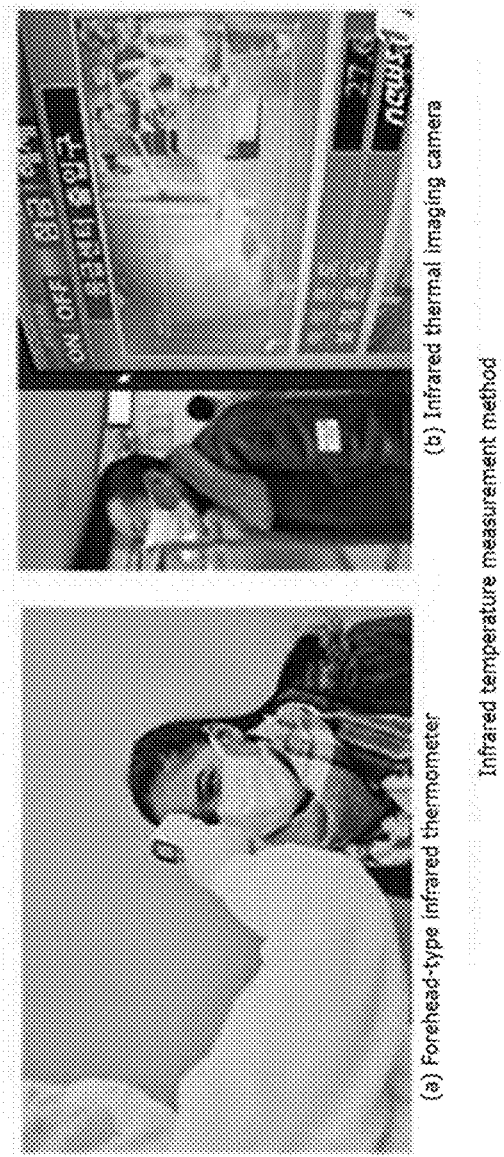
FIG. 2 shows an infrared temperature measurement method: (a) a forehead-type infrared thermometer, (b) a picture of an infrared thermal imaging camera.
Figure 3:
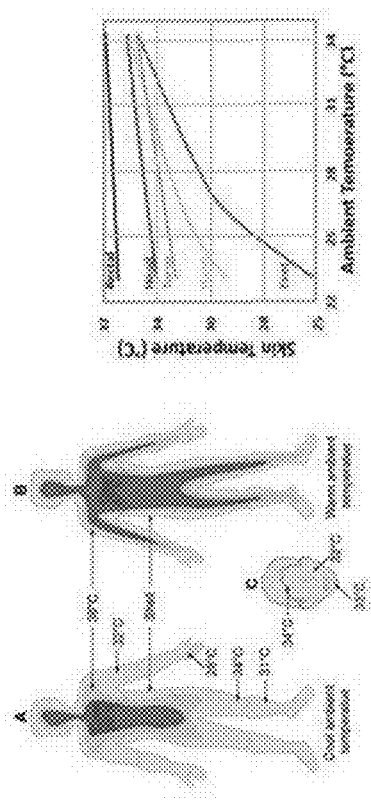
FIG. 3 is a drawing and a graph showing that as a method of measuring skin temperature of an infrared thermometer measures a different skin temperature for each part of a body, and the skin temperature of a human body changes as ambient temperature changes. Deviation thereof is shown to be different according to body parts, and the skin temperature deviates according to individual differences in the skin color or skin condition.
Figure 4:
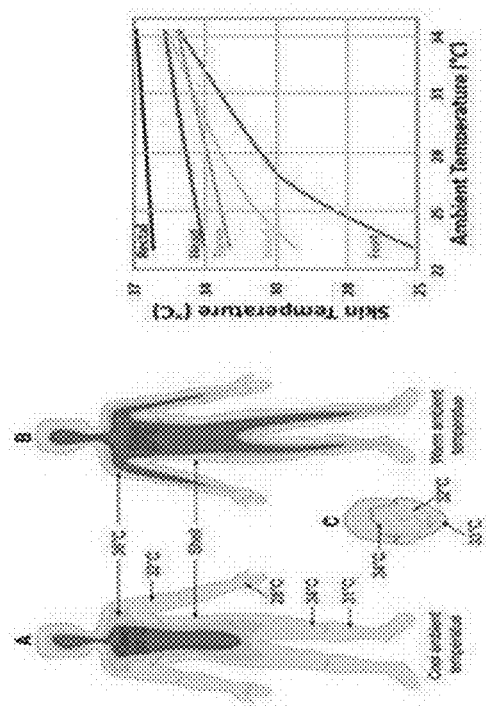
FIG. 4 is a view showing changes in the skin temperature and the core body temperature according to increase in the volume of body exercise.
Figure 5:
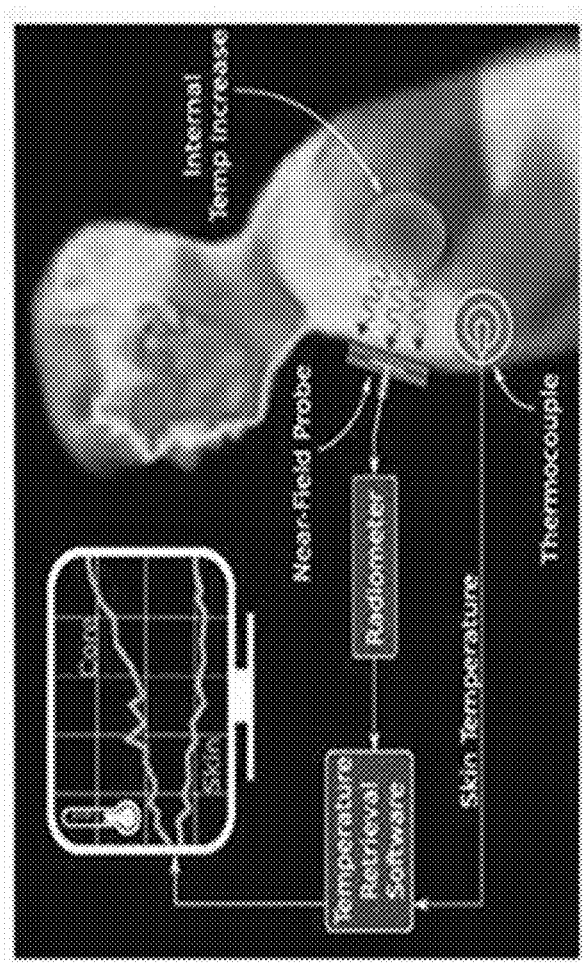
FIG. 5 is a conceptual view of an RF microwave core body thermometer equipped with a radiometric servo meter and an antenna.

FIG. 5 is a conceptual view of an RF microwave core body thermometer equipped with a radiometric servo meter and an antenna.

Figure 6:
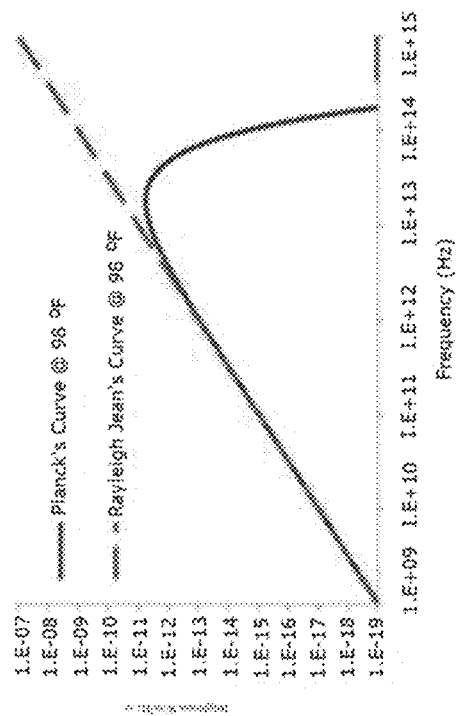
FIG. 6 is a graph showing an example (response characteristics when the body temperature is 98 degrees Fahrenheit) of the Planck's laws.
Figure 6:
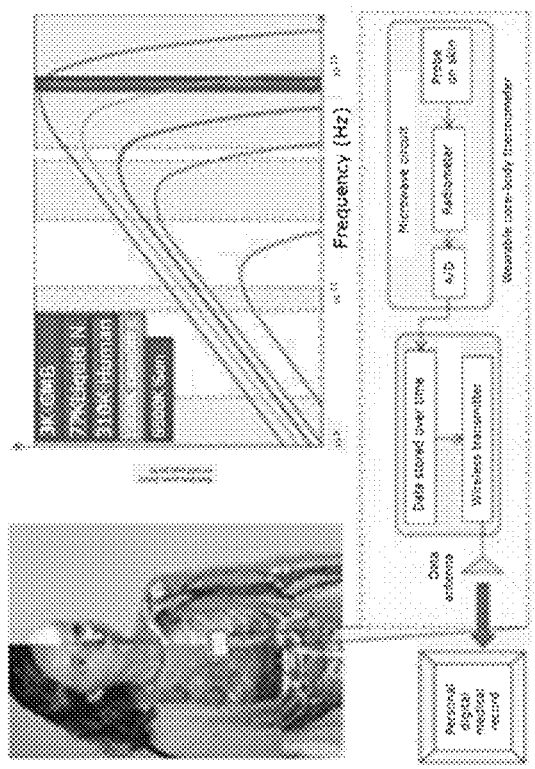

FIG. 6 is a graph showing an example (response characteristics when the body temperature is 98 degrees Fahrenheit) of the Planck's laws.

The RF microwave core body thermometer technique of the present invention uses a technique of converting a heat radiation signal radiated from the inside under the skin of a human body and transferred to the surface of the skin into a body temperature value by using a correlation between heat radiation power and bio-thermodynamic temperature.

Any one RF microwave frequency in an RF frequency range of 1 to 10 GHz is used to measure core body temperature inside a biological tissue of a human body, and in the RF microwave frequency range, electromagnetic waves penetrate up to 5 cm from the surface of skin tissue.

Within the RF frequency range of 1 to 10 GHz, core body temperature inside a human body may be measured by the power corresponding to the RF frequency by using the basic principle that radiation intensity changes almost linearly at an RF frequency lower than 10 GHz with respect to the core body temperature by the Plank and Rayleigh Jeans approximation law.

The RF receiver module of the RF microwave core body thermometer is a wearable core body thermometer attached to a human body, includes an RF contact-type patch antenna (near-field probe on skin), a radiometer, an ADC, a control unit, a storage unit, and a wireless transmitter, and measures core body temperature of a human body using any one RF frequency signal within an RF frequency range of 1 to 10 GHz.

In the embodiment, any one RF frequency of 1.8, 1.9, and 2.0 GHz frequencies is used as a specific RF frequency of the RF microwave core body thermometer.

Figure 7:
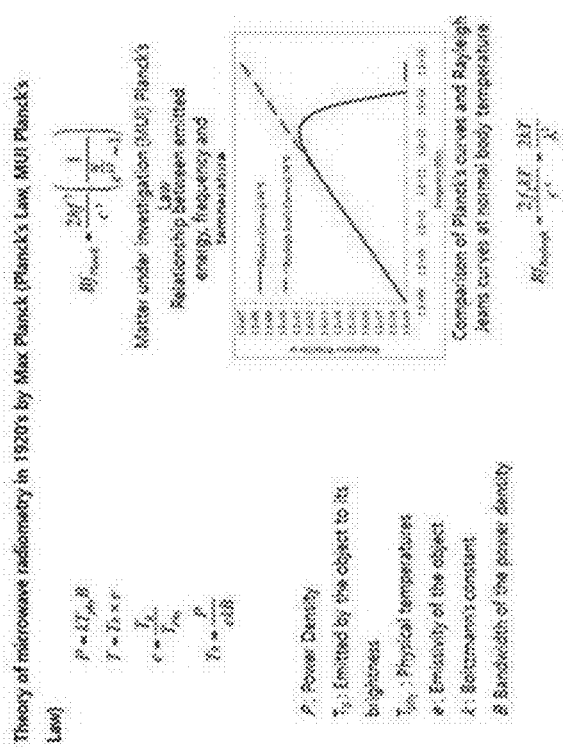
FIG. 7 is a view showing equations and a graph related to the RF microwave core body thermometer for the present invention.

FIG. 7 is a view showing equations and a graph related to the RF microwave core body thermometer for the present invention. According to the theory of microwave radiometry, a radiometer receives blackbody radiation in the form of propagating electromagnetic waves from an object with brightness temperature $T_B$ proportional to physical temperature and emissivity. The power that the antenna receives is proportional to the brightness temperature. The received power is a function of the frequency and bandwidth of a device, and the temperature and physical properties of a radiating medium. In a general application of the radiometry, incident power is in the form of a plane wave and received by the antenna.

Since microwave radiometers may sense temperature at a depth of up to 3 to 7 cm below the skin surface at microwave frequencies and determine a subsurface temperature, they are practical in the medical field. They are first applied to subsurface thermography.

Microwave radiometry for non-invasive temperature measurements is based on near-field power reception and makes it possible to achieve the spatial resolution and sensing depth required in various medical application fields including cancer detection.

Monitoring drug delivery for cancer treatment, hyperthermia temperature control, hypothermic neural rescue of infants suffering from hypoxia-ischemia, and detection of vesicoureteral reflux in children are used for non-invasive near-field radiometric measurements. As a non-invasive microwave thermometer detects arthritis, a method of measuring elevated joint temperature also has been investigated.

Antenna temperature of an object in near-field within a few centimeters using radiometry is a weighted average of the temperature of the objects close to the antenna. Therefore, weighting functions (WFs) are used to define an antenna.

A radiometer is a device for measuring incoherent radiation.

Power density $P = kT_{phy}B$

Temperature $T = T_B \times e$(brightness temperature $T_B \times$emissivity $e$)

Emissivity $e = \dfrac{T_B}{T_{phy}}$

Brightness temperature $T_B = \dfrac{P}{ekB}$

Here, P is power density, $T_B$ is brightness temperature emitted from an object, $T_{phy}$ is physical temperature, e is emissivity of the object, k is the Boltzmann's constant, and B is the bandwidth of the power density.

A radiometer is a device for measuring incoherent radiation, and Matter emits electromagnetic energy based on temperature of all directions with spectral brightness described by Planck's blackbody radiation law.

$$B_f = \dfrac{2hf^2}{c^2} \dfrac{1}{e^{hf/kT} - 1} \left[ W \cdot m^{-2} \cdot sr^{-1} \cdot Hz^{-1} \right] \quad \text{Equation (2)}$$

Here, h is Planck's constant ($6.63 \times 10^{-34}$ J·sec), c is the speed of light in vacuum (m/sec), k is Boltzmann's constant ($1.38 \times 10^{-23}$ J/K), and T is Kelvin temperature.

Referring to FIG. 7, it shows spectral brightness with respect to frequency for a temperature ranging from the cosmic microwave background (3K) to the temperature of the sun (6000K).

The brightness for microwave is different from the optical terminology of radiance.

$$B_f = \frac{2kTf^2}{c^2} = \frac{2kT}{\lambda^2} \quad \text{Equation (3)}$$

At a low frequency of hf/kT<<1, as a result, quantity ($e^{hf/kT}-1$) may be approximated by the truncated Taylor series like ($e^x-1\approx x$). The Planck's blackbody radiation law reduces the low frequency approximation known as Rayleigh-Jeans law.

In the case of body temperature ($\approx$310K), the Rayleigh-Jeans law deviates from the Planck's law by less than 1%. Since it is 127 GHz in maximum, it is effective in the microwave frequency range. Radiant electromagnetic energy may be received by an antenna that converts electromagnetic energy propagated as a guided wave of a transmission line in a free space by the Planck's blackbody radiation law.

Since the antenna is polarized and electromagnetic radiation has independent polarizations, the power received by the antenna from the spatial distribution of the spectral brightness given by Bf($\theta$, $\varphi$) will be only half of the total incident power.

Figure 8:
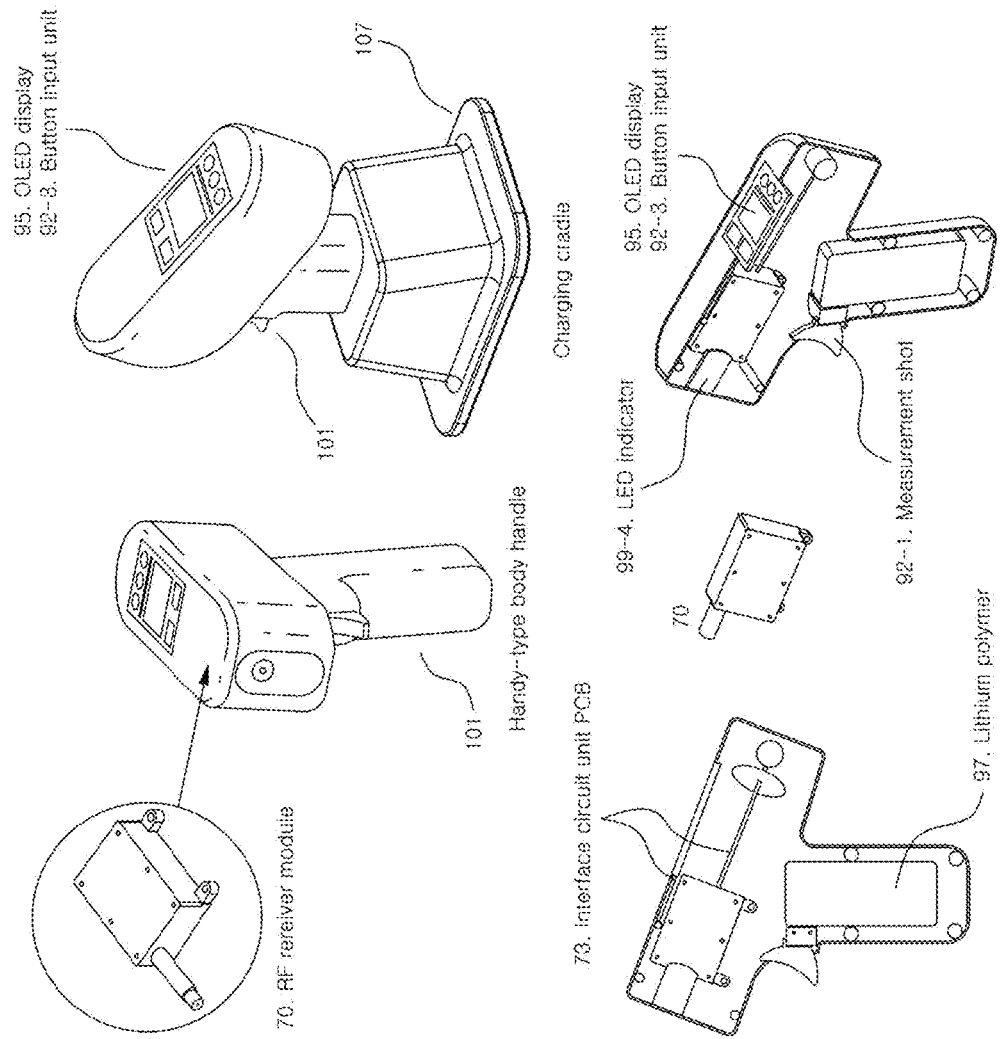
FIG. 8 is a picture showing a prototype of an RF microwave core body thermometer.

FIG. 8 is a picture showing a prototype of an RF microwave core body thermometer.

A product of the RF microwave core body thermometer includes an RF microwave core body thermometer 90 to 99 connected to the RF receiver module 70 for sensing core body temperature; a handy-type body equipped with the RF microwave core body thermometer 90 to 99 having the RF receiver module 70, connected to an interface circuit (PCB) of the RF receiver module 70, driven by a lithium polymer battery 97, included with an LED indicator 99-4 at the pistol-shaped entrance facing upward from the horizontal line at an angle of 30° or lower, included with a color OLED display 95 and a button input unit 92-3 on the top surface, and included with a measurement shot button 92-1 of the handle 101 of the pistol-shaped handy-type body; and a charging cradle 107 that mounts the handy-type body equipped with the RF microwave core body thermometer 90 to 99, is provided with an AC-DC converter, and is connected to an AC power plug to which an AC power line is connected.

A prototype of a handy-type RF microwave core body thermometer that can drive the "RF microwave transmission module", which is the core technology of the RF microwave core body thermometer, using a secondary battery (e.g., a lithium polymer battery) has been manufactured to secure base technology for commercialization.

An infrared thermometer is limited to measurement of temperature of skin surface such as the forehead, the back of a hand, the temple or the like, whereas the RF microwave core body thermometer may measure core body temperature in most of ranges including a chest, sides, and legs, and the center portion of a torso, and may measure both the front and rear sides of a body.

Figure 9:
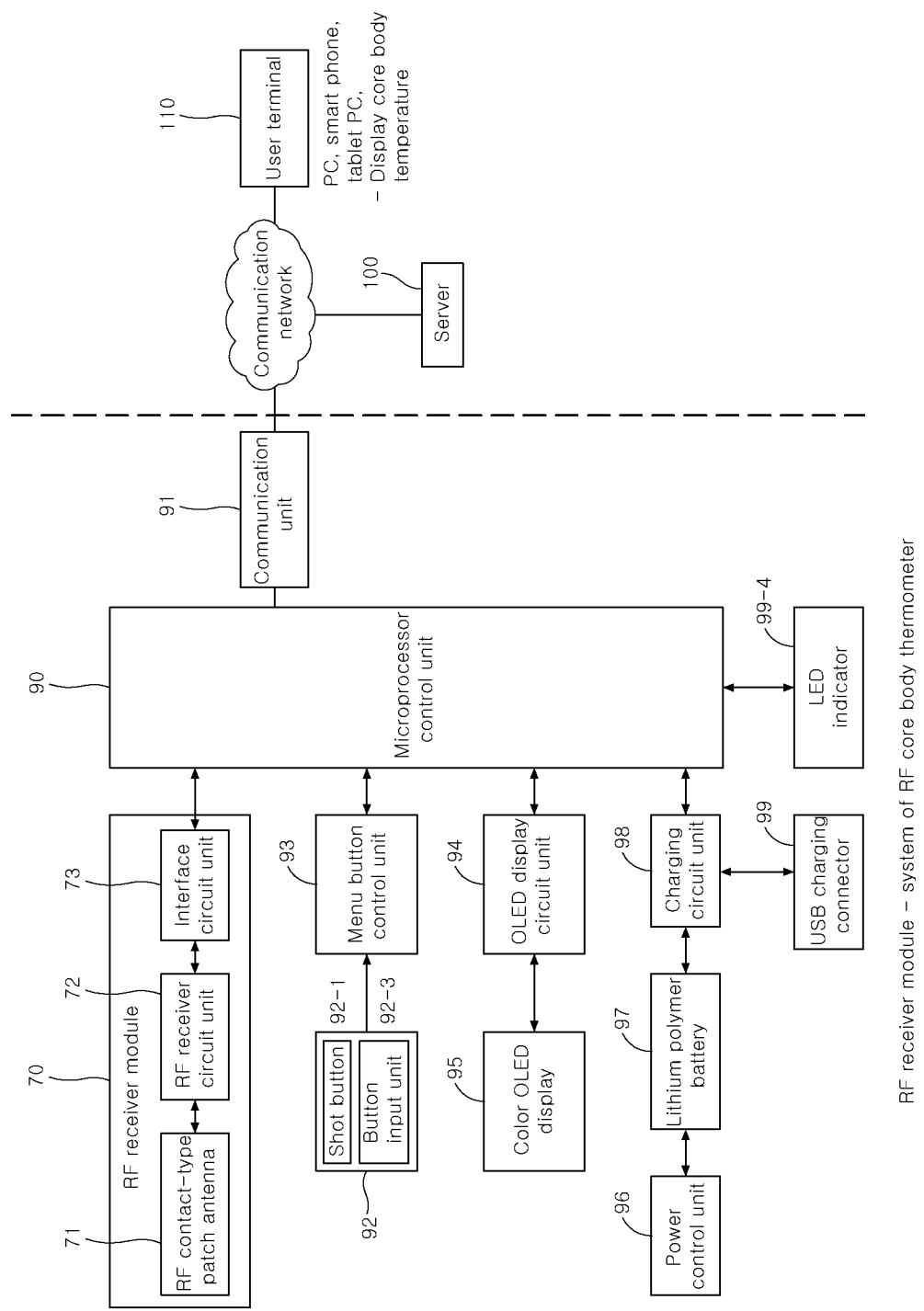
FIG. 9 is a block diagram showing an RF microwave core body thermometer provided with an RF receiver module for sensing core body temperature according to the present invention.

FIG. 9 is a block diagram showing an RF microwave core body thermometer provided with an RF receiver module for sensing core body temperature according to the present invention.

The RF microwave core body thermometer is provided with an RF receiver module for sensing core body temperature includes: an RF receiver module 70 for sensing core body temperature, which includes an RF receiver circuit unit 72 attached to a human body part to receive any one RF frequency signal within a frequency range of 1 to 10 GHz except for 1.4 GHz, 1.6 GHz, 1.7 GHz, 2.6 GHz and 2.7 GHz through an RF contact-type patch antenna 71 for sensing core body temperature, and an interface circuit unit 73; an RF microwave core body thermometer 90-99 connected to the interface circuit unit 73 of the RF receiver module 70 for sensing core body temperature in order to display the core body temperature of a human body measured by the power (watt (W), brightness) corresponding to the RF frequency using the basic principle that radiation intensity changes almost linearly at an RF frequency lower than 10 GHz with respect to the core body temperature inside the human body by the Planck's law by using any one RF frequency signal within a frequency range of 1 to 10 GHz, on an OLED display, wherein said one RF receiver module for sensing core body temperature, being included in an RF microwave core body thermometer, the module comprising: an RF contact-type patch antenna attached to a human body part to sense the core body temperature of the human body; an RF receiver circuit unit to receive any one RF frequency signal within a frequency range of 1 to 10 GHz except for 1.4 GHz, 1.6 GHz, 1.7 GHz, 2.6 GHz and 2.7 GHz through the RF contact-type patch antenna for sensing core body temperature and to be attached to a human body; and an interface circuit unit for connecting the RF receiver circuit unit to a control unit of a microprocessor control unit, wherein the thermometer further includes a handy-type body equipped with the RF microwave core body thermometer having the RF receiver module, connected to an interface circuit of the RF receiver module, driven by a lithium polymer battery, included with an LED indicator, included with a color OLED display and a button input unit on the top surface, and included with a measurement shot button of the handle of the pistol-shaped handy-type body.

The RF receiver module 70 for sensing core body temperature includes: an RF contact-type patch antenna 71 attached to a human body part to receive a heat radiation signal radiated from the inside under the skin of a human body and transferred to the surface of the skin; an RF receiver circuit unit 72 for receiving any one RF frequency signal within an RF frequency range of 1 to 10 GHz through the RF contact-type patch antenna 71; and an interface circuit unit 73 through which the RF receiver circuit unit 72 is connected to a microprocessor control unit 90, wherein the interface circuit unit includes an A/D converter for receiving the in-phase signal LO_I and its quadrature signal LO_Q of a local oscillator LO received from the RF receiver circuit unit, and A/D converting the signals; and a temperature converter for converting a heat radiation signal into a core body temperature inside a human body.

The RF microwave core body thermometer 90 to 99 includes a microprocessor control unit 90, a communication unit 91, a shot button input unit 92, a menu button control unit 93, an OLED display control unit 94, a color OLED display 95, a power control unit 96, a lithium polymer battery 97, a charging circuit unit 98, and a USB charging connector 99.

The RF microwave core body thermometer includes: a microprocessor control unit 90 connected to the interface circuit unit 73 of the RF receiver module 70 to control to convert a heat radiation signal radiated from the inside under the skin of a human body and transferred to the surface of the skin into a core body temperature value using a correlation between heat radiation power and bio-thermodynamic temperature within an RF frequency range of 1 to 10 GHz, and display a core body temperature inside the human body measured by the power corresponding to the RF frequency on a display using the basic principle that radiation intensity changes almost linearly at an RF frequency lower than 10 GHz with respect to the core body temperature inside the human body by the Planck's law; a button input unit 92 including a power ON/OFF button of the button input unit 92-3 of the display, and a measurement shot button 92-1; a menu button control unit 93 connected to the button input unit 92 to operate by the button; an OLED display control unit 94 and a color OLED display 95 connected to the microprocessor controller 90 to display the measured core body temperature of a human body; and a power control unit 96, a lithium polymer battery 97, a charging circuit unit 98, and a USB charging connector 99

Additionally or optionally, the RF microwave core body thermometer system further includes an LED indicator 99-4 connected to the microprocessor control unit 90 and provided at the pistol-shaped entrance.

The button input unit 92 includes a measurement shot button 92-1 pulled with an index finger from the hook of the pistol-shaped handle; and a button input unit 92-3 of a display provided adjacent to a color OLED display 95.

The communication unit 91 of the RF microwave core body thermometer 90 to 99 includes at least one communication unit among a Bluetooth communication unit, a Wi-Fi communication unit, an LTE 4G communication unit or 5G communication unit, and an IoT communication unit (LoRa RF communication unit or NB-IoT communication unit).

In addition, the RF microwave core body thermometer system further includes a user terminal 110 directly connected from the communication unit 91 of the RF microwave core body thermometer 90 to 99 through Wi-Fi or Bluetooth communication, and the user terminal displays core body temperature inside a human body measured by the power corresponding to the RF frequency. The user terminal 110 generates an alarm when the core body temperature exceeds a preset normal core body temperature by statistical data on each measurement part of a human body, and transmits a message to an emergency room system when the core body temperature excessively exceeds a preset core body temperature value.

The RF microwave core body thermometer system further includes: a server 100 for storing core body temperature inside a human body measured according to the power corresponding to the RF frequency received from the communication unit 91 of the RF microwave core body thermometer 90 to 99 through Wi-Fi, LTE 4G or 5G communication; and a user terminal 110 connected to the server 100 through a wired/wireless communication network (LAN, Ethernet, Wi-Fi, LTE 4G or 5G network) to display the core body temperature inside a human body stored in the server 100 and measured by the power corresponding to the RF frequency.

Any one among a smart phone, a tablet PC, a computer (PC), and an embedded system for a medical device is used as the user terminal 110.

An RF microwave frequency in a range of 1 to 10 GHz except for 1.4 GHz, 1.6 GHz, 1.7 GHz, 2.6 GHz and 2.7 GHz of the RF receiver module of the RF microwave core body thermometer is used to measure the core body temperature inside a biological tissue of a human body, and in the RF microwave frequency range, electromagnetic waves penetrate up to 3 to 7 Cm from the surface of skin tissue.

The RF microwave core body thermometer may measure deep core body temperature.

A core body temperature inside a human body by the power (brightness) corresponding to the RF frequency using the basic principle that radiation intensity changes almost linearly at an RF frequency lower than 10 GHz with respect to the temperature inside the human body (core body temperature) by the Planck's law so that a heat radiation signal radiated from the inside under the skin of the human body and transferred to the surface of the skin may be converted into a body temperature value by using a correlation between heat radiation power and bio-thermodynamic temperature within an RF frequency range of 1 to 10 GHz except for 1.4 GHz, 1.6 GHz, 1.7 GHz, 2.6 GHz and 2.7 GHz.

The RF receiver module of the RF microwave core body thermometer is a wearable core body thermometer attached to a human body, which includes an RF contact-type antenna (near-field probe on skin), a radiometer, an ADC, a control unit, a storage unit, and wireless transmitter, and measures core body temperature of a human body using an RF frequency signal within a frequency range of 1 to 10 GHz except for 1.4 GHz and 2.7 GHz.

In the embodiment, any one RF frequency of 1.8, 1.9, and 2.0 GHz frequencies is used as a specific RF frequency of the RF receiver module of the RF microwave core body thermometer.

Figure 12:
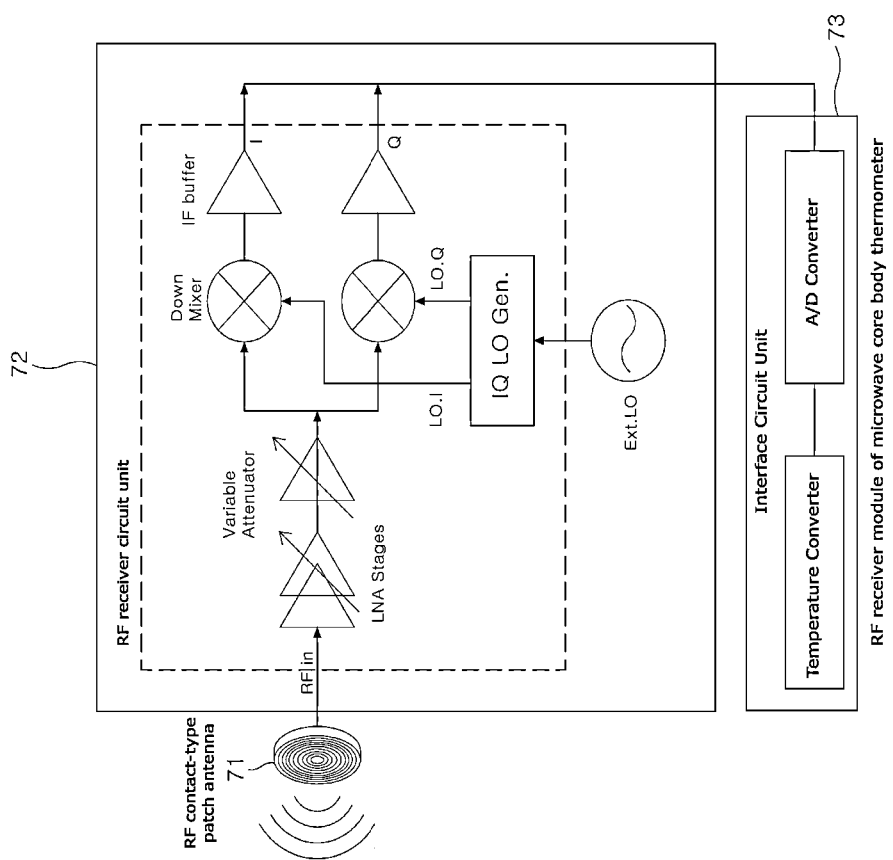
FIG. 12 is a view showing the design of an RF receiver module of a microwave core body thermometer. The antenna used in the core body thermometer minimizes ambient noise by using an RF contact-type short-range patch antenna.
Figure 10:
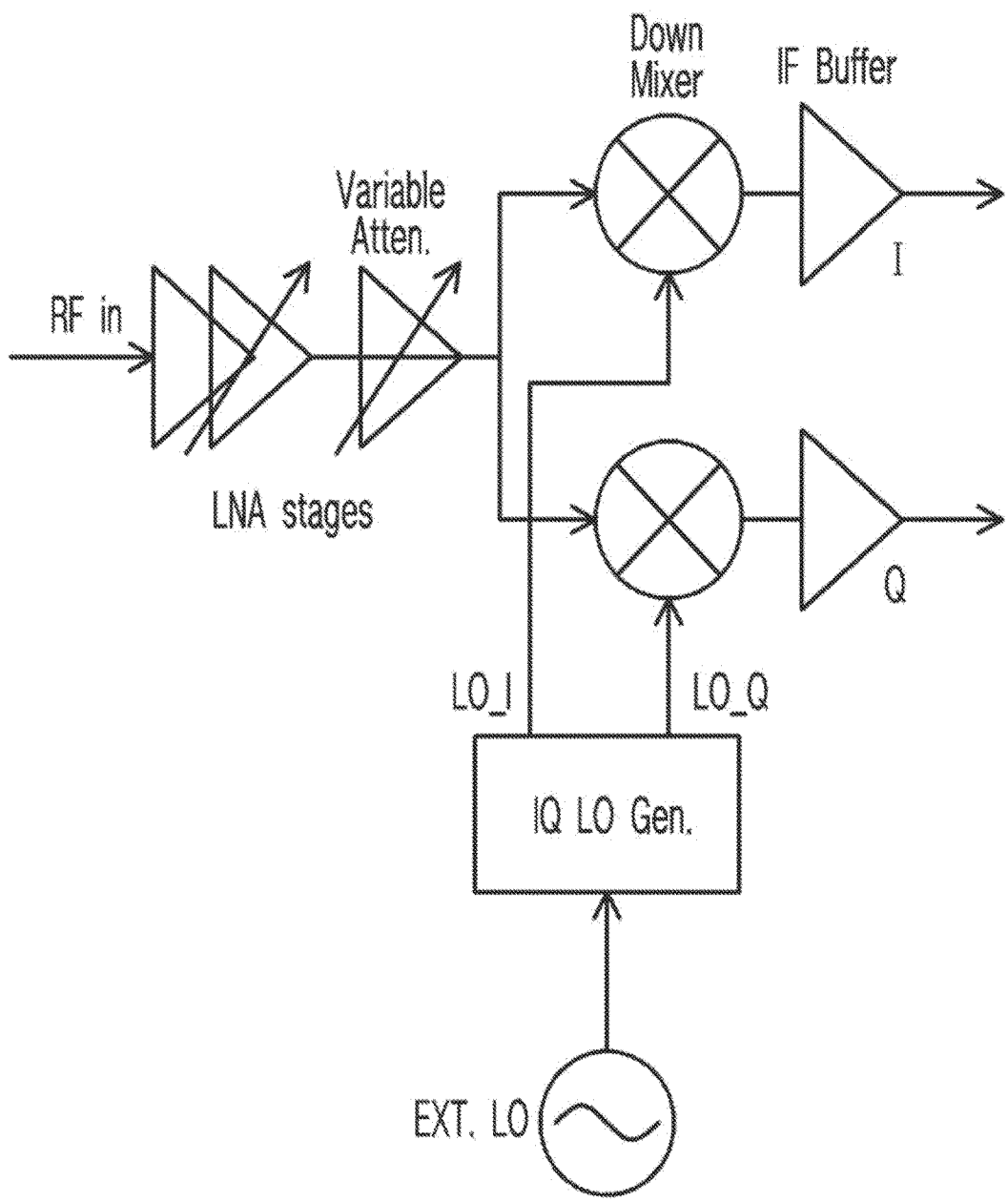

FIG. 12 is a view showing the design of an RF receiver module of a microwave core body thermometer.

The RF receiver module of the microwave core body thermometer is implemented on a silicon substrate as a CMOS chip, and the RF receiver module for sensing core body temperature includes: an RF contact-type patch antenna 71 attached to a human body to receive a heat radiation signal radiated from the inside under the skin of the human body and transferred to the surface of the skin; an RF receiver circuit unit 72; and an interface circuit unit 73.

The RF receiver circuit unit 72 includes: a low-noise amplifier stage (LNA stage) for receiving an RF frequency signal from the RF contact-type patch antenna 71, removing, for example, noise of a low voltage signal of 1.5 GHz within a frequency range of 1 to 10 GHz, and amplifying the low voltage signal; a variable attenuator connected to the low-noise amplifier stage to remove noise around the center frequency by attenuating the noise of the signal, and amplify the signal; two down mixers branched from the variable attenuator to down-convert the GHz frequency to an IF band frequency within a range of 50 to 200 MHz and improve sensitivity; two IF buffers connected to the two down mixers respectively to provide clean signals (I, Q) respectively by removing noise and resistance components of the down-converted IF frequencies; an on-chip oscillator (IQ LO generator) for oscillating a signal to make an amplitude-modulated sine wave in-phase and quadrature, and providing an in-phase signal LO_I and its quadrature signal LO_Q of the local oscillator LO; and an off-chip oscillator (Ext. LO) for providing an oscillation signal from the outside of the chip so that clock noise may not pass through from the outside of the chip.

The interface circuit unit 73 includes: an A/D converter for receiving the in-phase signal LO_I and its quadrature signal LO_Q of the local oscillator LO received from the RF receiver circuit unit 72, and A/D converting the signals; and a temperature converter for converting a heat radiation signal into a core body temperature inside a human body corresponding to a digital value measured by the power corresponding to the RF frequency using the basic principle that radiation intensity changes almost linearly at an RF frequency lower than 10 GHz with respect to the core body temperature inside a human body by the Planck's law, so that the heat radiation signal radiated from the inside under the skin of the human body and transferred to a surface of the skin may be converted into a body temperature value.

A/D converters of 32-bit, 64-bit, and 128-bit are used as the A/D converter.

Figure 10:
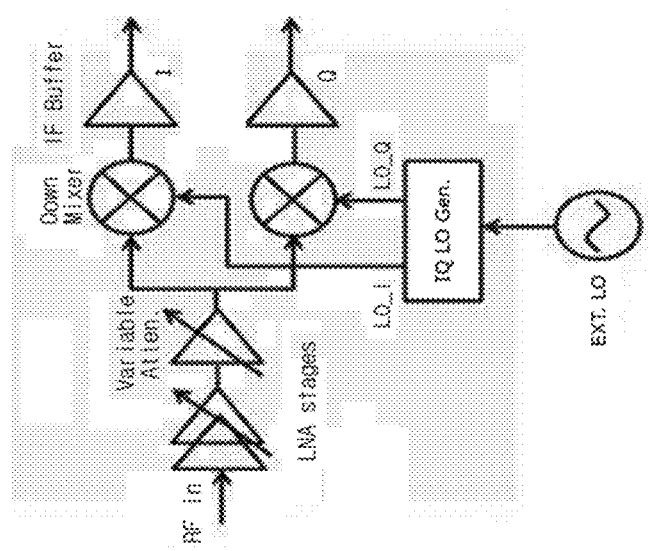
FIG. 10 is a view showing a structure of an MMIC chip on a silicon (Si) substrate for an RF receiver module of a core body thermometer manufactured by using a CMOS process to sense core body temperature.

FIG. 10 is a view showing a structure of an MMIC chip on a silicon (Si) substrate for an RF receiver module in an RF receiver module manufactured by using a CMOS process to sense core body temperature.

Figure 11:
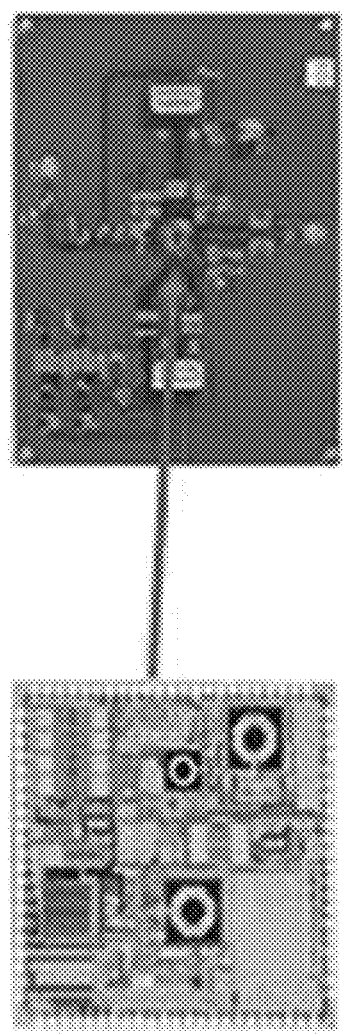
FIG. 11 is a picture showing a design of an RF receiver module for an RF receiver module of a core body thermometer, which is manufactured by using a CMOS process on a silicon (Si) substrate that will be developed.

FIG. 11 is a picture showing a design of an RF receiver module for an RF receiver module of a core body thermometer, which is manufactured by using a CMOS process on a silicon (Si) substrate for an RF receiver module of a core body thermometer that will be developed.

FIG. 12 is a view showing the design of an RF receiver module of a microwave core body thermometer. The antenna used in the core body thermometer minimizes ambient noise by using an RF contact-type short-range patch antenna.

1) Design of the structure and specifications of the RF receiver chip using a CMOS process for sensing core body temperature
- Review of required specifications of the RF receiver for sensing core body temperature, and an optimal RF/IF receiver
- Quantitative derivation of required specifications and design structure of a detailed circuit block utilizing an RF receiver M&S (Modeling & Simulation) method based on the required specifications and a selected RF receiver structure 2) Design and development of an RF/IF circuit of a broadband RF receiver chip of 1 to 2 GHz
- Design of an RF front end circuit of the RF receiver module, including a low-noise amplifier (LNA) and down mixers for low noise, high gain, and easy gain control in a broadband of 1 to 2 GHz
- Design of an LO generation circuit including VCO for LO generation of 1.1 to 1.7 GHz
- Design of an IF stage circuit unit including circuits of an amplifier and a sensing unit including low noise, high gain, and gain control functions at the center frequency of 250 MHz
- Integration of the designed RF, LO, IF circuits, and optimization design of integrated performance of the entire RF receiver 3) Layout and fabrication of an RF/IF receiver MMIC chip using a CMOS process
- Design and fabrication of an RF receiver module on a silicon (Si) substrate by using a CMOS process through a CMOS circuit layout process and a post layout simulation of each detailed RF, IF, and LO circuit units of an RF/IF receiver chip manufactured as a single chip using a CMOS process
- Layout design and overall performance review of a single receiver chip integrating the layouts of detailed circuit blocks
- An MMIC chip (RF/IF receiver chip) of the RF receiver module is manufactured as one chip using the System Integration Package/Chip technology on silicon (Si) substrate by using a CMOS process 4) Manufacturing and verification of a test board of the RF receiver chip and module
- Design of a circuit diagram and a layout of a test board for performance evaluation of the manufactured RF receiver module
- Manufacture of a test board using an RF receiver module through a CMOS process, and measurement of required specifications (measuring and verifying specifications such as gain, NF, P1 dB, IP3, spurious suppression, power consumption, etc.)

RF microwave core body thermometers provided with an RF receiver module that overcomes the fundamental limit of existing infrared sensors measuring skin temperature and measures core body temperature inside a human body are localized and supplied to the digital healthcare and medical fields.

The present invention manufactures one MMIC chip on a silicon (Si) substrate for an RF receiver module for measuring core body temperature as one chip in an RF receiver module by using a CMOS process and an RF microwave core body thermometer having the same, and provides an RF microwave core body thermometer system having an RF/IF receiver module that measures core body temperature inside a human body by using any one RF frequency signal within an RF frequency range of 1 to 10 GHz.

An infrared thermometer is limited to measurement of temperature of skin surface such as the forehead, the back of a hand, the temple or the like, whereas the RF microwave core body thermometer may measure core body temperature in most of ranges including a chest, sides, and legs, and the center portion of a torso, and may measure both the front and rear sides of a human body.

An RF microwave core body thermometers, in which an RF receiver module that overcomes the fundamental limit of existing infrared sensors measuring skin temperature and measures core body temperature inside a human body is manufactured as an MMIC chip, are localized and supplied to the digital healthcare and medical fields.

Although it has been described with reference to specific embodiments of the present invention, the present invention is not limited to the configuration and operation described in the specific embodiments to illustrate the technical spirit as described above, and it can be implemented to be diversely modified within the limit not departing from the technical spirit and scope of the present invention. Therefore, such modifications should be regarded as belonging to the scope of the present invention, and the scope of the present invention should be determined by the claims described below.

What is claimed is:

1. A radio frequency (RF) receiver module for sensing core body temperature, the RF receiver module being included in an RF microwave core body thermometer, the module comprising:
   an RF contact-type patch antenna attached to a human part to sense the core body temperature of the human body;
   an RF receiver circuit unit to receive any one RF frequency signal within a frequency range of 1 to 10 GHz except for 1.4 GHz, 1.6 GHz, 1.7 GHz, 2.6 GHz and 2.7 GHz through the RF contact-type patch antenna for sensing core body temperature and to be attached to a human body; and
   an interface circuit unit for connecting the RF receiver circuit unit to a control unit of a microprocessor control unit,
   wherein the interface circuit unit includes:
   an A/D converter configured to receive, from the RF receiver circuit unit, an in-phase signal LO_I and its quadrature signal LO_Q of a local oscillator LO, and A/D convert the in-phase signal and its quadrature signal; and a temperature converter configured to convert a heat radiation signal into a core body temperature inside the human body.

2. The module according to claim 1, wherein a specific RF frequency of the RF receiver module for sensing the core body temperature measures the core body temperature of the human body by using any one RF frequency of 1.8, 1.9, and 2.0 GHz frequencies.

3. The module according to claim 1, wherein the RF receiver circuit unit includes:

a low-noise amplifier (LNA) stage for receiving an RF frequency signal from the RF contact-type patch antenna, removing noise of a low voltage signal within a frequency range of 1 to 10 GHz, and amplifying the low voltage signal;

a variable attenuator connected to the low-noise amplifier stage to remove noise around the center frequency by attenuating the noise of the signal, and amplify the signal;

two down mixers branched from the variable attenuator to down-convert the GHz frequency into an IF band frequency within a range of 50 to 200 MHz and improve sensitivity;

two IF buffers connected to the two down mixers respectively to provide clean signals (I, Q) respectively by removing noise and resistance components of the down-converted IF frequencies;

an on-chip internal oscillator (IQ LO generator) for oscillating a signal to make an amplitude-modulated sine wave in-phase and quadrature, and providing the in-phase signal LO_I and its quadrature signal LO_Q of the local oscillator LO; and an off-chip external oscillator (Ext. LO) for providing an oscillation signal from the outside of the chip so that clock noise may not pass through from the outside of the chip.

4. The module according to claim 3, wherein the temperature converter is configured to convert the heat radiation signal into the core body temperature inside the human body corresponding to a digital value measured by power corresponding to an RF frequency by using a basic principle that radiation intensity linearly changes at an RF frequency lower than 10 GHz with respect to the core body temperature inside the human body by a Planck's law, so that the heat radiation signal radiated from the inside under a skin of the human body and transferred to a surface of the skin may be converted into a body temperature value.

5. The module according to claim 1, wherein in the RF receiver module for sensing core body temperature, an MMIC chip is provided on a silicon (Si) substrate for the RF receiver module.

6. A radio frequency (RF) microwave core body thermometer system having one RF receiver module for sensing core body temperature, the thermometer comprising:

said one RF receiver module for receiving any one RF frequency signal within an RF frequency range of 1 to 10 GHz except for 1.4 GHz, 1.6 GHz, 1.7 GHz, 2.6 GHz and 2.7 GHz, and sensing the core body temperature; and an RF microwave core body thermometer connected to an interface circuit unit of said one RF receiver module in order to display a core body temperature inside a human body measured by power corresponding to an RF frequency by using a basic principle that radiation intensity linearly changes at an RF frequency lower than 10 GHz with respect to a core body temperature inside the human body by a Planck's law by using the received RF frequency signal, on an organic light-emitting diode (OLED) display, wherein said one RF receiver module for sensing core body temperature, being included in an RF microwave core body thermometer, the module comprising: an RF contact-type patch antenna attached to the human body to sense the core body temperature of the human body; an RF receiver circuit unit to receive any one RF frequency signal within a frequency range of 1 to 10 GHz except for 1.4 GHz, 1.6 GHz, 1.7 GHz, 2.6 GHz and 2.7 GHz through the RF contact-type patch antenna for sensing core body temperature and to be attached to the human body; and an interface circuit unit for connecting the RF receiver circuit unit to a control unit of a microprocessor control unit, and wherein the thermometer further includes a handy-type body equipped with the RF microwave core body thermometer having the RF receiver module, connected to an interface circuit of the RF receiver module, driven by a lithium polymer battery, included with an LED indicator, included with a color OLED display and a button input unit on the top surface, and included with a measurement shot button of the handle of the pistol-shaped handy-type body.

7. The thermometer system according to claim 6, wherein in the RF receiver module for sensing core body temperature, an MMIC chip is provided on a silicon (Si) substrate for the RF receiver module.

8. The thermometer system according to claim 6, wherein the RF microwave core body thermometer includes:

a microprocessor control unit connected to the interface circuit unit of the RF receiver module to control to convert a heat radiation signal radiated from the inside under the skin of the human body and transferred to the surface of the skin into a core body temperature value using a correlation between heat radiation power and bio-thermodynamic temperature within an RF frequency range of 1 to 10 GHz, and display a core body temperature inside the human body measured by the power corresponding to the RF frequency on a display by using the basic principle that radiation intensity linearly changes at an RF frequency lower than 10 GHz with respect to the core body temperature inside the human body by the Planck's law;

a communication unit connected to the microprocessor control unit;

a button input unit including a power ON/OFF button of a button input unit of a display, and a measurement shot button;

a menu button control unit connected to the button input unit to operate by the button;

an OLED display control unit and a color OLED display connected to the microprocessor controller to display the measured core body temperature of the human body; and a power control unit, a secondary battery, a charging circuit unit, and a USB charging connector.

9. The thermometer system according to claim 8, further comprising an LED indicator connected to the microprocessor control unit and provided at a pistol-shaped entrance.

10. The thermometer system according to claim 6, further comprising:

a charging cradle that mounts the handy-type body equipped with the RF microwave core body thermometer, is provided with an AC-DC converter, and is connected to an AC power plug connected a power cable.

11. The thermometer system according to claim 6, further comprising a user terminal directly connected from a communication unit of the RF microwave core body thermometer through Wi-Fi or Bluetooth communication,
   wherein the user terminal displays core body temperature inside the human body measured by the power corresponding to the RF frequency.

12. The thermometer system according to claim 6, further comprising:
   a server for storing core body temperature inside the human body measured according to the power corresponding to the RF frequency from a communication unit of the RF microwave core body thermometer; and
   a user terminal connected to the server through a wired/wireless communication network to display the core body temperature inside the human body stored in the server which is measured by the power corresponding to the RF frequency.

13. The thermometer system according to claim 12, wherein the user terminal uses any one of a smart phone, a computer, a personal computer (PC), a tablet PC, or an embedded system for a medical device.

\* \* \* \* \*

UNITED STATES PATENT AND TRADEMARK OFFICE
CERTIFICATE OF CORRECTION

PATENT NO. : 11,737,674 B2
APPLICATION NO. : 17/169447
DATED : August 29, 2023
INVENTOR(S) : Nam Young Kim, Eun Seong Kim and Jaewoo Shin Page 1 of 2

It is certified that error appears in the above-identified patent and that said Letters Patent is hereby corrected as shown below:

In the Drawings

Please replace Fig. 10 with Fig. 10 as shown on the attached page.

Signed and Sealed this
Nineteenth Day of August, 2025

Coke Morgan Stewart
*Acting Director of the United States Patent and Trademark Office*

Design of structure and specifications of MMIC chip in CMOS RF receiver module for sensing core body temperature